United States Patent [19]

Barle et al.

[11] Patent Number: 4,796,621
[45] Date of Patent: Jan. 10, 1989

[54] PROTECTIVE SURGICAL FACE MASK

[76] Inventors: Louis Barle, 109 Fenwood Dr., Old Saybrook, Conn. 06475; Ron Vliet, 376 Wells Rd., Wethersfield, Conn. 06109

[21] Appl. No.: 130,301

[22] Filed: Dec. 9, 1987

[51] Int. Cl.[4] ............................................. A61F 9/00
[52] U.S. Cl. ........................... 128/206.23; 128/206.21; 128/206.19
[58] Field of Search ............ 128/206.23, 206.24, 128/206.25, 206.26, 206.13, 206.14, 206.16, 206.19; 52/171

[56] References Cited

U.S. PATENT DOCUMENTS

| | | | |
|---|---|---|---|
| 2,056,753 | 10/1936 | Wagner | 128/206.19 |
| 2,353,978 | 7/1944 | Weber | 52/171 |
| 2,400,720 | 5/1946 | Staudinger et al. | 52/171 |
| 3,834,384 | 9/1974 | Raines | 128/206.14 |
| 3,971,369 | 7/1976 | Aspelin et al. | 128/206.19 |
| 4,248,220 | 2/1981 | White | 128/206.19 |
| 4,296,746 | 10/1981 | Mason, Jr. et al. | 128/206.24 |

Primary Examiner—Edgar S. Burr
Assistant Examiner—Kimberly L. Asher
Attorney, Agent, or Firm—McCormick, Paulding & Huber

[57] ABSTRACT

A surgical, protective face mask includes a lower portion of sheet material which conforms to the facial characteristics of a wearer to cover the mouth and nose and includes an opening in the region of the eyes having an anatomically contoured covering made of a transparent optical grade plastic material and forms a seal along its periphery to protect the openings of the eye from invasive entry of viral infectious fluids and the like while permitting the wearer to wear spectacles in the normal manner.

11 Claims, 2 Drawing Sheets

PROTECTIVE SURGICAL FACE MASK

BACKGROUND OF THE INVENTION

The present invention relates generally to protective face masks and deals more specifically with a protective face mask for preventing the evasive entry of fluids or other particulates and the like into the openings of the mouth, nose and eyes of a wearer.

It has recently been found that a number of contagious diseases, in particular, infectious viral diseases such as, Acquired Immune Deficiency Syndrome (AIDS), are transmitted via bodily fluids. As a result, health agencies, such as the Center for Disease Control, have recommended that surgeons, dentists and other medical personnel protect themselves from the invasive entry of such fluids through the mucus membranes of the mouth, nose and eyes which may arise during the performance of their duties when treating individuals having such contagious diseases.

In addition to medical personnel, other professionals such as veterinarians, laboratory workers, chemical handlers, painters, and others exposed to hazardous or poisonous materials require protection of the openings of the mouth, nose and eyes from invasive entry of foreign fluids and materials.

One major problem generally associated with protective masks such as disclosed in U.S. Pat. No. 2,056,753 issued to Wagner, Oct. 6, 1936, is the inability to wear spectacles in the normal manner.

Another problem with protective face masks of the above-referenced general type is the inability to use medical appliances of the type that cooperate with spectacles or ones having eye pieces requiring close proximity to the eye of the user. Such appliances, typically, are representative of appliances used during microsurgery.

Yet another problem generally associated with protective masks of the above-referenced type is the difficulty encountered in attempting to wipe the spectacles during the progress of an operation since the mask is worn over the spectacles.

It is an object therefore, of the present invention, to provide a total surgical protective face mask which prevents the invasive entry of fluids and the like into the mucus membranes of the mouth, nose and eyes while permitting the user to wear spectacles in the normal manner.

SUMMARY OF THE INVENTION

In accordance with the present invention, a mask for covering the face to prevent the invasive entry of fluids, particulates and the like into the mucus membranes of the mouth, nose and eyes of a user includes a lower portion of sheet material having means for conforming the shape of the material to cover the mouth and nose of a user and includes an opening in the region of the eyes at an upper portion of the sheet material and further includes means for covering the opening with a transparent, plastic sheet material of substantial equal thickness. The plastic sheet material is anatomically contoured to cover the facial area in the region of the eyes to permit a user to wear a pair of spectacles in the normal manner outside the covering means. Additionally, means in the form of an elastic fabric band or a tie permit attachment of the mask to the head of the user.

The invention further resides in the anatomically contoured covering extending generally transversely across the brow from ear-to-ear near the temples and contouring convexly downward from an upper edge and at both sides of the bridge portion of the nose toward a region just below the cheekbone and then extending generally inward toward the fleshy portion of the face in the region of the cheekbone and terminating at a lower edge. An absorbent barrier material is attached to and located along the periphery of the contoured covering and forms a seal between the covering and the face of a user when the mask is worn.

BRIEF DESCRIPTION OF THE DRAWINGS

Other features and advantages of the present invention will become readily apparent from the following description and drawings wherein.

DETAILED DESCRIPTION OF THE PREFERRED EMBODIMENTS

Figure 6:
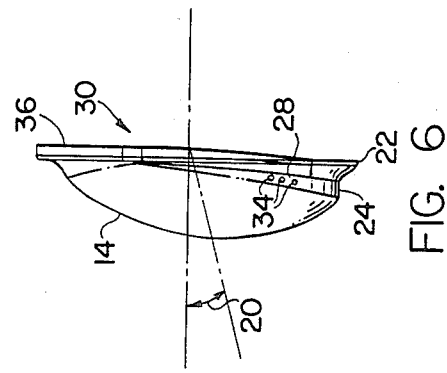
FIG. 6 is a schematic side view of the anatomically contoured protective covering.
Figure 3:
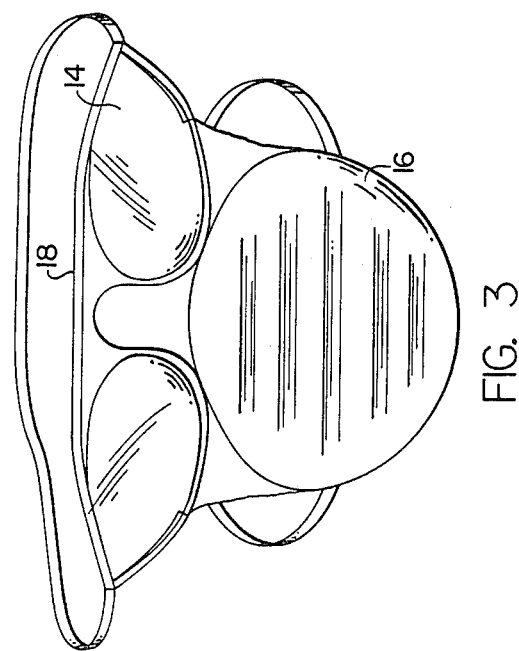
FIG. 3 is a schematic, front view of the surgical face mask embodying the present invention wherein the lower portion comprises a molded composition portion for covering the nose and mouth.
Figure 2:
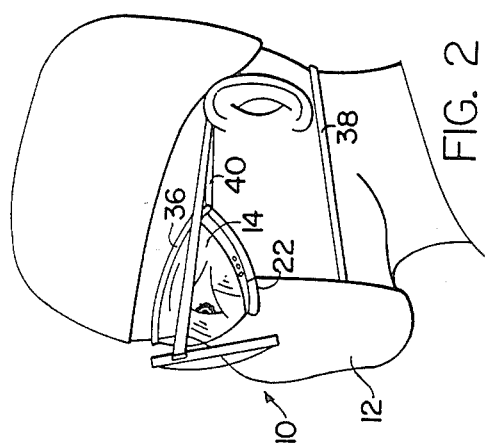
FIG. 2 is somewhat schematic side view of a user wearing the face mask of the present invention and having spectacles showing the anatomically contoured portion behind the spectacles.
Figure 1:
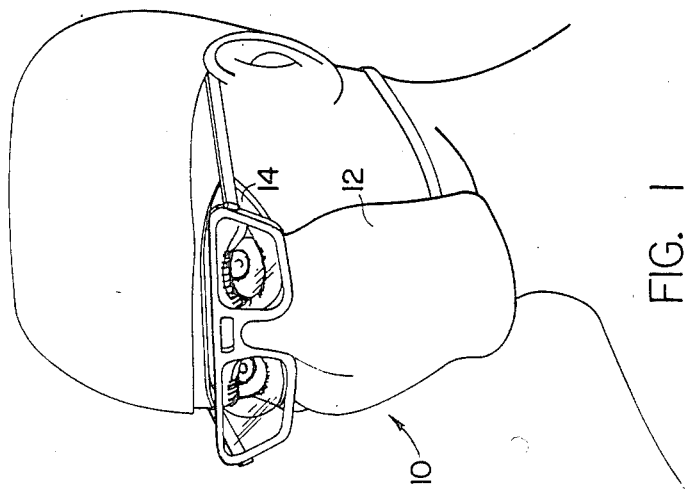
FIG. 1 is a somewhat perspective view of the face mask of the present invention shown as worn by a user having spectacles.
Figure 5:
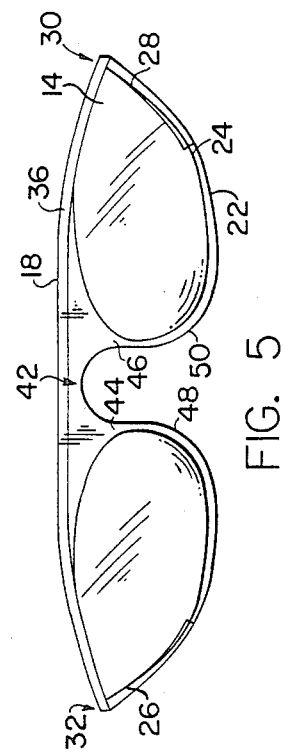
FIG. 5 is a more detailed, somewhat schematic front view of the anatomically contoured protective covering.
Figure 4:
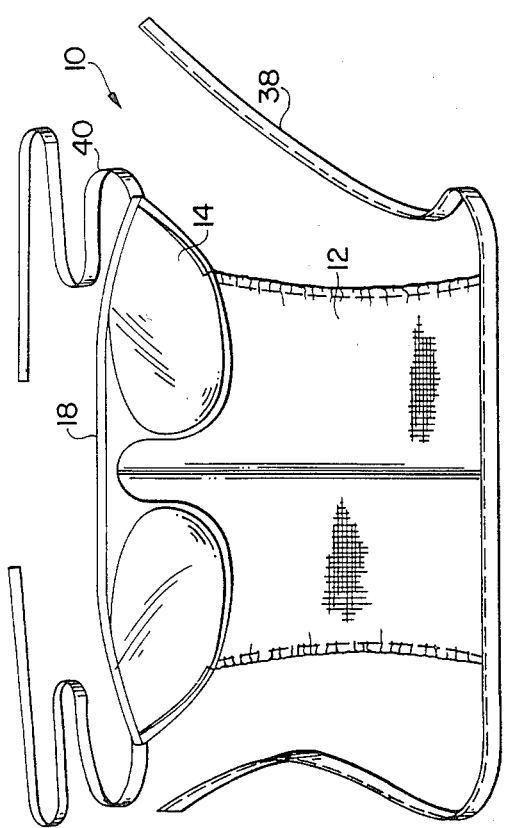
FIG. 4 is a somewhat schematic, front view of the surgical face mask embodying the present invention wherein the lower sheet material comprises a pleated fabric composition material for covering the nose and mouth of a wearer.
Figure 7:
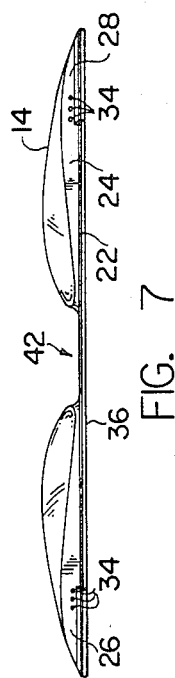
FIG. 7 is a schematic bottom view of the anatomically contoured protective covering illustrating the ventilation openings.

Turning now to the drawings, the protective, surgical face mask embodying the present invention is shown generally in the drawings as 10 and comprises a lower portion 12 of sheet material of the general type utilized in conventional surgical masks covering just the mouth and nose of a wearer. The material is generally pleated to allow expansion and conformance to the facial features of an individual wearer when the mask is worn. The sheet material includes an opening in the region of the eyes at an upper portion of the sheet material. An anatomically contoured covering 14 is attached to the sheet material 12 and covers the opening to form the face mask.

The lower portion of the face mask may also be made from a moldable or plasticized preformed cup-shaped mask of the type well known in the industry and designated 16 in the drawings.

The anatomically contoured covering is attached to the opening in the sheet material in any well known manner taking into account the composition of the sheet material and the material of the covering. In the present invention, the anatomically contoured covering 14 is made of a thermoplastic material, preferably an optical grade plastic and having a substantially equal thickness to insure distortion free vision and no optical attenuation. The shape of the anatomically contoured covering 14 is such that an upper edge 18 extends generally transversely across the brow from ear-to-ear near the temples and follows generally along a line running just above the eyebrows and the bridging portion of the brow between the eyebrows. The covering extends convexly from the upper edge 18 of the covering toward the sheet material 12 to provide clearance for eyelashes of a user when wearing the mask. The convex shape in this region of the contoured covering is such to provide distortion free vision up to and including at least 15° as indicated by the angle 20 as shown in FIG. 6. The shape of the covering is particularly contoured and optically designed to permit a user to wear bifocals. Beyond the region of the the 15° (degrees) curvature, the covering extends generally inward toward the fleshy portion of the face in the region in the cheekbone and terminates at a lower edge 22 and forms a somewhat flatter portion 24 along the lower portion of the covering 14. The flattened portion 24 further includes an area designated generally 26 and 28 near the temple region 30 and 32 respectively of the covering 14.

A plurality of ventilation apertures 34,34 extend through the covering 14 to prevent the covering from fogging when worn by a user. Alternately, the thermo plastic material comprising the covering may be chemically treated using any well known defogging chemical intended for this purpose and which treatment process is well known to those skilled in the art.

An absorbent tape material 36 is attached to and located substantially along the periphery of the inner portion of the contoured covering 14 to provide a seal between the covering 14 and the facial surface of a user when the mask is worn. The absorbent material 36 prevents liquids, perspiration, or contaminated fluid and other particulates from dripping or running into the region in the eyes thus preventing any contact of such fluids with the mucus membranes in the openings of the eyes, nose and mouth.

The surgical protective face mask 10 is attached to a wearer's head by elastic fabric bands 38 and 40. The elastic band 38 is attached to the lower portion of the mask 10, and when the mask is worn, urges the periphery of the lower portion of the mask into contact with the facial surface to provide a tight seal. The elastic band 40 is attached to the temple region of the contoured covering 14 and when the mask is worn by a user urges the contoured covering into contact with the facial surface so that the absorbent material 36 forms a seal along the periphery of the contoured covering. It will be understood that the elastic fabric bands 38 and 40 may be ties or other well known attachment means commonly made in the industry.

The bridge portion 42 and the areas 44 and 46 of the contoured covering 14 extend in a U-shaped fashion from the upper edge 18 in the area of the bridge section 42 and at either side of the bridge of a nose so that when the mask 10 is worn by a user, the portion of the lens covering 14 at either side of the nose come into contact with the facial surface area defined by the juncture formed by the area between the eye socket and the nose and is identified by the areas designated 48 and 50 respectively. The width across the bridge of the nose is sufficiently wide to accomodate the bridge of an spectacle frame so that the nose pads rest on sheet material coveering the bridge of the nose of a wearer thereby permitting the spectacles to be worn in the normal manner.

A surgical, protective face mask is described above by way of example in several preferred embodiments. Accordingly, it will be understood that numerous changes and modifications may be had to those skilled in the art without departing from the spirit and scope of the invention and therefore the invention has been described by way of illustration rather than limitation.

We claim:

1. A mask for covering the face to prevent invasive entry of fluids, atomized particles and the like into the openings of the mouth, nose and eyes, said mask comprising:

a lower portion of sheet material having means for conforming the shape of the material to cover the mouth and nose of a user and an opening in the region of the eyes at an upper portion of said sheet material including means for covering the eye opening with a transparent plastic sheet material of substantially constant thickness throughout wherein the plastic sheet material is anatomically contoured to extend generally transversely across the brow and substantially from temple to temple and downward from an upper edge and at both sides of the bridge portion of the nose to a region of the face defined by the cheekbone and generally inward toward the fleshy portion of the face and terminating in a lower edge to cover the facial area in the region of the eyes and permit a user to wear spectacles in the normal manner outside the covering means, and first means secured to the lower portion of the sheet material and second means secured to the anatomically contoured covering in the upper portion of the sheet material for attaching the mask to the head of a user.

2. A mask as defined in claim 1 wherein said anatomically contoured covering includes a top edge extending generally transversely across the brow from ear-to-ear near the temples and following generally along a line running just above the eyebrows and bridging the portion of the brow between the eyebrows, said covering contouring convexly downward from the top edge and at both sides of the bridge portion of the nose toward a region just below the cheekbone thereby providing clearance for the eyelashes of a user and then extending generally inwardly toward the fleshy portion of the face in the region of the cheekbone and terminating at a lower edge, said lower edge being contoured from the temple area to the bridge area of the nose to approximate the general shape of the face of a user.

3. A mask as defined in claim 2 further including absorbent barrier material means attached to and located along the periphery of said contoured covering and forming a seal between said contoured covering and the face of a user when the mask is worn.

4. A mask as defined in claim 2 wherein said contoured covering is shaped to provide distortion free vision up to and including at least 15° from horizontal vision to permit the mask to be worn by a user having bifocal spectacles.

5. A mask as defined in claim 2 further including means for defogging said contoured covering when the mask is worn by a user.

6. A mask as defined in claim 5 wherein said defogging means includes ventilation openings extending completely through said contoured covering in the inwardly extending portion of said covering and closest to the temple area of said contoured covering.

7. A mask as defined in claim 5 wherein said defogging means includes said contoured covering being made of a transparent plastic sheet material treated with a defogging chemical.

8. A mask as defined in claim 1 wherein said sheet material of said lower portion comprises a paper fabric material.

9. A mask as defined in claim 1 wherein said sheet material of said lower portion comprises a preformed, cup-shaped covering.

10. A mask as defined in claim 1 wherein said first and second attachment means comprises an elastic fabric band.

11. A mask as defined in claim 1 wherein said transparent plastic sheet material is an optical grade plastic.

* * * * *